United States Patent [19]

Steudle et al.

[11] Patent Number: 5,011,826
[45] Date of Patent: Apr. 30, 1991

[54] AQUEOUS DIALYSIS AND RINSING SOLUTION FOR INTRAPERITONEAL ADMINISTRATION

[75] Inventors: Volker Steudle; Volker Bartz, both of Giessen, Fed. Rep. of Germany

[73] Assignee: Fresenius AG, Bad Homburg, Fed. Rep. of Germany

[21] Appl. No.: 335,921

[22] Filed: Apr. 10, 1989

[30] Foreign Application Priority Data

Apr. 15, 1988 [DE] Fed. Rep. of Germany ....... 3812525

[51] Int. Cl.$^5$ ........................ A61K 9/08; A61K 31/70; A61K 33/06; A61K 33/14
[52] U.S. Cl. ........................... 514/23; 536/1.1; 424/677; 424/682; 424/722; 435/1
[58] Field of Search ............................ 514/23; 536/1.1; 424/677, 682, 722; 435/1

[56] References Cited

U.S. PATENT DOCUMENTS

| | | | |
|---|---|---|---|
| 3,911,915 | 10/1975 | Seifter et al. | 514/23 |
| 4,308,255 | 12/1981 | Raj et al. | 424/678 |
| 4,574,085 | 3/1986 | Dolkart et al. | 514/23 |
| 4,880,629 | 11/1989 | Okamoto et al. | 514/23 |

FOREIGN PATENT DOCUMENTS

WO82/03773 11/1982 World Int. Prop. O. ............ 514/23

*Primary Examiner*—Ronald W. Griffin
*Assistant Examiner*—Nancy S. Carson
*Attorney, Agent, or Firm*—Jack Schuman

[57] ABSTRACT

Peritoneal dialysis solution with usual electrolyte composition in physiological amounts and with galactose as osmotically active substance in an amount of 1-70 g/l.

13 Claims, No Drawings

AQUEOUS DIALYSIS AND RINSING SOLUTION FOR INTRAPERITONEAL ADMINISTRATION

DESCRIPTION

The invention relates to the use of galactose as osmotically active substance in intraperitoneal dialysis and rinsing or irrigating solutions.

In patients with acute or chronic renal insufficiency the restricted kidney function must be compensated by alternative methods. For this purpose in practice two methods are employed: hemodialysis and peritoneal dialysis. In hemodialysis the blood of the patients is cleaned extracorporeally with the aid of an artificial semipermeable membrane. In peritoneal dialysis the peritoneum serves as semipermeable membrane. The dialysis solution is introduced via a catheter into the peritoneal cavity.

From U.S. Pat. No. 4,308,255 a hypertonic solution is known which can be used as dialysate for hemodialysis and peritoneal dialysis for patients suffering from loss of kidney function and which is intended to shorten the time necessary for washing out toxic substances in peritoneal dialysis. This solution contains 2-10% by weight dextran in addition to sodium, chloride, bicarbonate or lactate or acetate in predetermined quantity ratios. It may also possibly contain up to 5% by weight dextrose and up to 15 mg zinc gluconate.

A central purpose of a dialysis solution for renal insufficiency patients is on the one hand to absorb excess water and substances usually eliminated with the urine and on the other hand to supply substances which for metabolic reasons occur in insufficient concentration in the organism (electrolyte balance). The water extraction in peritoneal dialysis is by osmotically active substances such as glucose, fructose, sugar alcohols and derivatives or other unphysiological substances, and until this day no "optimum" osmotically active substance has been found. After a certain equilibration time, i.e. after concentration-dependent exchange of substances of the dialysis with the blood, the "used" dialysis solution is drained from the peritoneal cavity and replaced by new solution. Further requirements made of a dialysis solution are a composition from as far as possible physiological components, i.e. components occurring naturally in a healthy organism, to obtain the highest possible biocompatibility and avoid further pathophysiological changes, e.g. accumulation of unphysiological or non-metabolizable substances, in the organism. Further biocompatibility parameters are that the osmotically active substance does not exhibit any systemic or peritoneal toxicity, does not inhibit local immune defense mechanisms, exhibits no immune toxicity, and exhibits rapid metabolization after absorption with the slowest possible absorption rate and physiological pH and osmolarity ranges.

A further requirement of a peritoneal dialysis solution is that for the patient a positive nutritive effect should be achieved. Of practical significance are carbohydrates and amino acids, in particular with regard to the daily protein loss of the patients of 5-10 g to the dialysate.

By far the most widespread is the use of glucose as osmotically active substance. The disadvantages are in particular that glucose is metabolized by almost all microorganisms and this increases the danger of peritonitis of microbial origin. In the peritoneal washing of diffuse peritonitides with glucose-containing solutions there is specifically an overproportional increase in the risk of Candida infections. Furthermore, glucose is easily absorbed from the peritoneal cavity. The blood glucose concentration is increased (hyperglycemia) resulting in increased insulin concentration (hyperinsulinemia) which can manifest itself in fat metabolism disturbances (hyperlipemia) and diabetes mellitus. With diabetic patients specifically the problems known from enteral nutrition are encountered from the start PCT-PA WO 83/00087 discloses an aqueous solution for peritoneal dialysis which is distinguished in that the monomeric sugars occurring in conventional solutions of this type, such as glucose and fructose, or dimeric sugars, such as saccharose or maltose, are replaced by metabolizable carbohydrate polymers having an average polymerization degree of at least 4; preferably, the carbohydrate polymer is a glucose polymer having an average polymerization degree of 4 to 10.

The decrease in the osmolarity of the dialysis solution during the course of the peritoneal dialysis method is to be less in the presence of such carbohydrate polymers than with conventional dialysis solutions containing monosaccharides or disaccharides.

Although when using fructose, to be considered physiological like glucose, as osmotically active substance the problems of hypoglycemia are avoided (nutrition of diabetics), irritations of the peritoneum frequently occur.

The latter are also possible when using the dialysis solution which is known from PCT-PA WO 82/03773 and which contains an aqueous solution of physiological salts in a concentration adequate for physiological compatibility with blood and a mixture of physiological amino acids with insulin in proportions sufficient to permit the essential assimilations of said amino acids by a patient. This solution can also contain a source of carbohydrate nutrition, for example glucose, glucose polymers, fructose or a sugar alcohol; other carbohydrates are not named. The insulin is intended to achieve that the metabolization of the amino acids and glucose present if desired, which diffuse from the dialysis solution into the blood stream of the patient, is facilitated.

In addition, increased plasma fructose levels, in particular with increased blood glucose levels (diabetes mellitus), lead via the polyol path to an increase in the fructose concentration in the lens tissue of the eye. Since in contrast to glucose fructose cannot again leave the lens tissue by permeation, the increase of the fructose concentration can assume such dimensions that osmotically active concentrations are reached. This leads to an increased water influx to the lens tissue with swelling and disturbance of the optical properties and the latter can finally lead to the clinical picture of lens opacification (diabetic cataract).

After infusions of fructose solutions in parental feeding, lactate acidosis, drop in the energy-rich phosphates in the liver, and a rise of the plasma uric acid levels can be observed. These metabolism disturbances, which are dramatic in particular for renal insufficiency patients, are caused by fructose being broken down faster than glucose in the liver. The phosphorylation to fructose-1-phosphate causes a drop in the adenosine triphosphate (ATP) and activated phosphate concentration ($P_i$), the ATP drop activating the 5-nucleotidase and the $P_i$ drop activating the adenosine monophosphate (AMP) desaminase. Consequently, increased inosine is formed for purine synthesis and uric acid. An increase in the uric acid level (hyperuricemia) leads to the specific disease picture known as gout and distinguished by deposits of urate in the joints and other tissues.

At present other osmotically active substances play only a secondary role in peritoneal dialysis solutions, in particular because due to their unphysiological character (except for amino acids and peptides) negative long-term effects are observed which are due mainly to the metabolization after absorption being too low or too slow. To be mentioned here are hyperosmolar plasma states when using the sugar alcohol sorbite and xylite, cumulation of glucose polymers and glycerin, allergic reactions with gelatin and toxicity of synthetic polymers. Substances with higher molecular weight (hydroxyethyl starch, dextrans, albumin) further exhibit a smaller osmotic effectiveness than smaller molecules so that to obtain a correspondingly high water extraction (ultrafiltration) very high concentrations must be used and these can lead to shock reactions (dextran shock). When using amino acids there is the danger of induction of amino acid imbalances with metabolic pathomechanism which can in the long term have a negative effect on the nutritional state of the patients. In particular for renal insufficiency, an optimum amino acid composition with other substances is still to be found. In addition, technical problems are encountered in the sterilization of amino acids or peptides together with reducing sugars as calorie carriers by formation of toxic substances (Maillard reaction).

Then there is a major problem in peritoneal dialysis, peritonitis complications, which frequently lead to breaking off the therapy: said substances are excellent substrates for relevant microorganisms. In particular when using peritoneal washing for post-operative diffuse peritonitides increased mycotic infections (v.a. Candida albicans) lead to enormous difficulties because of invasive intraperitoneal fungal growth.

The problem underlying the invention is to make available osmotically active dialysis and washing or rinsing solutions which can be administered to patients over long periods of time intraperitoneally without complications due to osmotic phenomena occurring; the microbial and peritoneal-dialytic complications occurring hitherto with known dialysis and washing solutions are to be reduced and adequate withdrawal of water and substances otherwise eliminated in the urine ensured, as well as a correction of the electrolyte balance. Furthermore, a contribution to covering the calorie requirement is to be ensured.

This problem is solved by the dialysis and rinsing solution according to the invention for intraperitoneal administration which is characterized by an aqueous solution having a galactose content of 1-70 g/l as osmotically active substance.

The following advantages are achieved when using galactosecontaining dialysis solutions according to the invention:

Galactose is the monosaccharide which is most similar biochemically to glucose. The chemical properties, empirical formula and thus the molecular weight are identical, as are the absorption mechanisms. In the liver galactose is converted to glucose and can thus be metabolized more easily.

This means delayed occurrence of glucose in the blood and this avoids glucose peaks. This is a considerable advantage in the case of patients dependent on insulin.

The physiological properties, technical handling and, as is particularly important, the osmotic activity correspond to those of glucose. Thus, when using galactose instead of glucose as osmotically active substance all the positive properties known in this respect for glucose are achieved without the disadvantages of glucose. Occurrence of hyperglycemia with the resulting hyperinsulinemia is substantially reduced because the conversion of galactose to glucose in the liver is controlled depending upon the need. Also avoided are excessive blood glucose concentrations as inductor for diabetes mellitus and hyperlipemias.

Increased plasma galactose levels caused by galactosecontaining peritoneal dialysis solution are physiological in contrast to the majority of hitherto employed osmotically active peritoneal dialysis solutions. For galactose occurs physiologically in large quantities in the enzymatic cleavage of milk sugar (lactose)—the sole carbohydrate serving for nutrition of the juvenile organism—consisting of one molecule each of the monosaccharides glucose and galactose.

A particular advantage, above all in tropical countries, is the fact that galactose in contrast to glucose is not a substrate for Candida albicans. Galactose is not metabolized by Candida albicans. Consequently, the dreaded mycotic infections are avoided.

In contrast to fructose, galactose does not accumulate in the eye lens tissue. The inosite and uric acid production is not stimulated.

In contrast to sugar alcohols, glycerin, disaccharides and oligosaccharides, gelatins or other high-valency carbohydrates, galactose is parentally absorbed and completely metabolized. There is no cumulation and as osmotically active substance galactose does not develop any toxicity in peritoneal dialysis.

The new dialysis solution includes the same components as already known peritoneal dialysis solutions with the exception that the osmotically active substance, such as glucose, is partially or completely replaced by galactose.

The galactose concentrations used depend on the mixed osmolar pressure and lie in the range from 1-70 g/l for peritoneal dialysis solutions. Advantageously, they are in the range from 5-50, in particular 16-25 g/l. Galactose is an easily obtainable commercial product. It is available commercially as highly pure galactose with a purity degree of more than 99%. It is obtained in practice by enzymatic or acidic hydrolysis of lactose.

The new dialysis solution can be prepared by the known processes for preparing glucose-containing dialysis solutions.

If as further optional osmotically active substance the dialysis solution according to the invention contains glucose in addition to galactose, the quantity ratio is advantageously 1:3 to 3:1, preferably 1:1. The dialysis solution may however if desired contain not only glucose but also for example fructose, sorbite, xylite, glycerin, modified gelatins, carbohydrates, amino acids and/or peptides as further optional osmotically active substance(s).

The electrolyte salts can be present in known manner in the form of the acetate, lactate, chloride and/or bicarbonate.

The ion concentrations in the dialysis solution according to the invention are advantageously 125-150, in particular 132-140 mmol/l $Na^+$; 0-8, in particular 0-4 mmol/l $K^+$; 0-3, in particular 0.5-2 mmol/l $Ca^{++}$; 0-2.5, in particular 0.3-1 mmol/l $Mg^{++}$; 10-60, in particular 30-50 mmol/l ions, selected from the group lactate, acetate and bicarbonate ions, the remainder $Cl^-$.

The osmotic pressure of the dialysis solution according to the invention is advantageously 300-700, in particular 320-550, preferably 350-450 mosm/l. An example for a usual additive which may be present in the dialysis solution if desired is insulin.

EXAMPLE 1

In 1 liter water of injection quality a solution of 16.5 g galactose and electrolyte salts in the form of the lactate and chloride is prepared.

| | |
|---|---|
| $Na^+$ | 132.0 mmol/l |
| $Ca^{++}$ | 1.75 mmol/l |
| $Mg^{++}$ | 0.75 mmol/l |
| $Cl^-$ | 102.0 mmol/l |
| Lactate$^-$ | 35.0 mmol/l |
| Galactose monohydrate | 16.5 g/l |

The solution is filtered and sterilized. The theoretical osmotic pressure is 355 mosm/l.

EXAMPLE 2

Example 1 was repeated with the exception that 46.75 g/l galactose monohydrate was used. Theoretical osmotic pressure: 507 mosm/l.

What is claimed is:

1. Aqueous dialysis and rinsing solution for intraperitoneal administration containing electrolytes, an osmotically active substance and optional additives, characterized in that galactose is the sole osmotically active substance and is present in a concentration of 1-70 g/l.

2. Solution according to claim 1, characterized by an osmotic pressure in the range from 300 to 700 mosm/l.

3. Solution according to claim 1, characterized by an osmotic pressure in the range from 320 to 450 mosm/l.

4. Solution according to claim 1, characterized by an osmotic pressure in the range from 350 to 450 mosm/l.

5. Solution according to claim 1, characterized by a galactose concentration of 5-50 g/l.

6. Solution according to claim 1, characterized by a galactose concentration of 16-25 g/l.

7. Solution according to claim 1, characterized by a concentration of 125-150 mmol/l $Na^+$, 0-8 mmol/l $K^+$, 0-3 mmol/l $Ca^{++}$, 0-2.5 mmol/l $Mg^{++}$, and 10-60 mmol/l ions selected from the group consisting of lactate ions, acetate ions and bicarbonate ions, and chloride ions in an amount sufficient to make the solution electrically neutral.

8. Solution according to claim 1, characterized by a concentration of 132-140 mmol/l $Na^+$, 0-4 mmol/l $K^+$, 0.5-2 mmol/l $Ca^{++}$, 0.3-1 mmol/l $Mg^{++}$, and 30-50 mmol/l ions selected from the group consisting of lactate ions, acetate ions and bicarbonate ions, and chloride ions in an amount sufficient to make the solution electrically neutral.

9. Aqueous dialysis and rinsing solution for intraperitoneal administration containing electrolytes, osmotically active substances and optional additives, characterized in that galactose and glucose are the sole osmotically active substances and are present in a total concentration of 1-70 g/l.

10. Solution according to claim 9, characterized in that the galactose:glucose ratio is 1:3-3:1.

11. Solution according to claim 10, characterized in that the galactose:glucose ratio is 1:1.

12. Aqueous dialysis and rinsing solution for intraperitoneal administration comprising electrolytes and an osmotically active substance, characterized by a concentration of 132.0 mmol/l $Na^+$, 1.75 mmol/l $Ca^{++}$, 0.75 mmol/l $Mg^{++}$, 102.0 mmol/l $Cl^-$, 35.0 mmol/l lactate and 16.5 g/l galactose monohydrate as the sole osmotically active substance.

13. Aqueous dialysis and rinsing solution for intraperitoneal administration comprising electrolytes and an osmotically active substance, characterized by a concentration of 132.0 mmol/l $Na^+$, 1.75 mmol/l $Ca^{++}$, 0.75 mmol/l $Mg^{++}$, 102.0 mmol/l $Cl^-$, 35.0 mmol/l lactate and 46.75 g/l galactose monohydrate as the sole osmotically active substance.

* * * * *